United States Patent
Popp et al.

(10) Patent No.: US 6,395,115 B1
(45) Date of Patent: May 28, 2002

(54) PROCESS FOR MAKING A GARMENT WITH DUAL REFASTENABLE SIDES AND BUTT SEAMS

(75) Inventors: Robert Lee Popp, Hortonville; Joseph D. Coenen, Neenah; Jack L. Couillard, Menasha; Christopher Peter Olson, Neenah; David Arthur Kuen, Neenah; Shawn A. Quereshi, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/571,348

(22) Filed: May 16, 2000

(51) Int. Cl.$^7$ .......................... A61F 13/56; A61F 13/64
(52) U.S. Cl. ...................... 156/66; 156/226; 156/227; 156/256; 156/270; 156/290; 156/292; 156/304.1; 156/304.6; 156/308.4; 604/387; 604/390; 604/391
(58) Field of Search ........................ 156/66, 226, 227, 156/290, 291, 292, 304.1, 304.6, 308.4, 256, 266, 269, 270; 604/386–391

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,772,120 A | 11/1973 | Radzins |
| 3,802,817 A | 4/1974 | Matsuki et al. |
| 3,849,241 A | 11/1974 | Butin et al. |
| 4,340,563 A | 7/1982 | Appel et al. |
| 4,663,220 A | 5/1987 | Wisneski et al. |
| 4,704,116 A | 11/1987 | Enloe |
| 4,940,464 A | 7/1990 | Van Gompel et al. |
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman |
| 5,374,262 A | 12/1994 | Keuhn, Jr. et al. |
| 5,386,595 A * | 2/1995 | Kuen et al. ..................... 2/111 |
| 5,830,206 A | 11/1998 | Larsson |
| 6,328,725 B2 * | 12/2001 | Fernfors ..................... 156/217 |

FOREIGN PATENT DOCUMENTS

| | | |
|---|---|---|
| EP | 0 217 032 | 4/1987 |
| WO | 95/27462 | 10/1995 |
| WO | 97/23180 | 7/1997 |

* cited by examiner

*Primary Examiner*—Sam Chuan Yao
(74) *Attorney, Agent, or Firm*—Pauley Petersen Kinne & Erickson

(57) ABSTRACT

A method of producing refastenable side seams in an absorbent garment results in an absorbent garment that is adapted to easy application and removal. The refastenable side seams can be produced in either a cross direction or a machine direction. Each of the refastenable side seams is a dual side seam that includes a standing butt seam formed between a front lap seam and a back lap seam. The resulting garment can be opened and closed on either a front side of the garment or a back side of the garment.

12 Claims, 5 Drawing Sheets

PROCESS FOR MAKING A GARMENT WITH DUAL REFASTENABLE SIDES AND BUTT SEAMS

FIELD OF THE INVENTION

This invention is directed to a process for making pant-like, personal care absorbent products having hook and loop fasteners on the side panels for ease of removal and donning without complete removal of a wearer's clothing.

BACKGROUND OF THE INVENTION

Pant-like absorbent garments, such as adult incontinence wear as well as infant and children's diapers, swim wear and training pants, typically have adhesive fasteners on the sides for donning and removal, or else rely on the waist opening and leg openings to slide on and off the wearer. Adhesive fasteners wear out in as little as one use. Therefore, if a care giver checks the status of the wearer's absorbent garment contents by unfastening an adhesive fastener, the garment often must be replaced due to a worn out adhesive fastener even if the absorbent garment itself is not in need of changing.

Absorbent garments that slide on and off a wearer are often messy when full. Furthermore, in order to remove such absorbent garments, the wearer's clothing covering the absorbent garments, such as pants, must be completely removed. Checking the status of the wearer's absorbent garment contents is often just as cumbersome as changing the absorbent garment.

There is a need or desire for a process for making pant-like, personal care absorbent garments that have refastenable side seams for ease of removal and donning without complete removal of a wearer's clothing.

SUMMARY OF THE INVENTION

The present invention is directed to a process for making pant-like absorbent garments having hook and loop fasteners applied at the sides of the garments. The process can be carried out in either the cross direction or in the machine direction. In the process of the invention, a fastening component is attached to each of two front side panels and to each of two back side panels of the garment assembly. A mating fastening component, wider than the fastening components, is placed over each fastening component. The garment assembly is then folded such that each mating fastening component on the front side panels is either face-to-face or back-to-back with a fastening component on the back side panels. A portion of each mating fastening component is then bonded to the adjacent mating fastening component at a distal edge of the mating fastening components. The bonded distal edges form standing butt seams.

The resulting absorbent garments have refastenable seams and can be easily fitted to and removed from a wearer without complete removal of a wearer's clothing. The refastenable side seams extend from a waist opening to each of two leg openings between a front panel and a back panel, and are "dual-sided" such that the garment can be unfastened at either the front panel or the back panel. Each of the refastenable side seams includes a fastening component and a mating fastening component, each of which comprises either a hook material or a loop material. The refastenable side seams experience a shearing strain during use, as opposed to peel forces, thereby reducing the likelihood of the seams opening unexpectedly.

With the foregoing in mind, it is a feature and advantage of the invention to provide a process for making a pant-like absorbent garment that can be easily applied to and easily removed from a wearer without the need to entirely remove the wearer's clothing.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" which refers to the length of a fabric in the direction in which it is produced.

Figure 3:
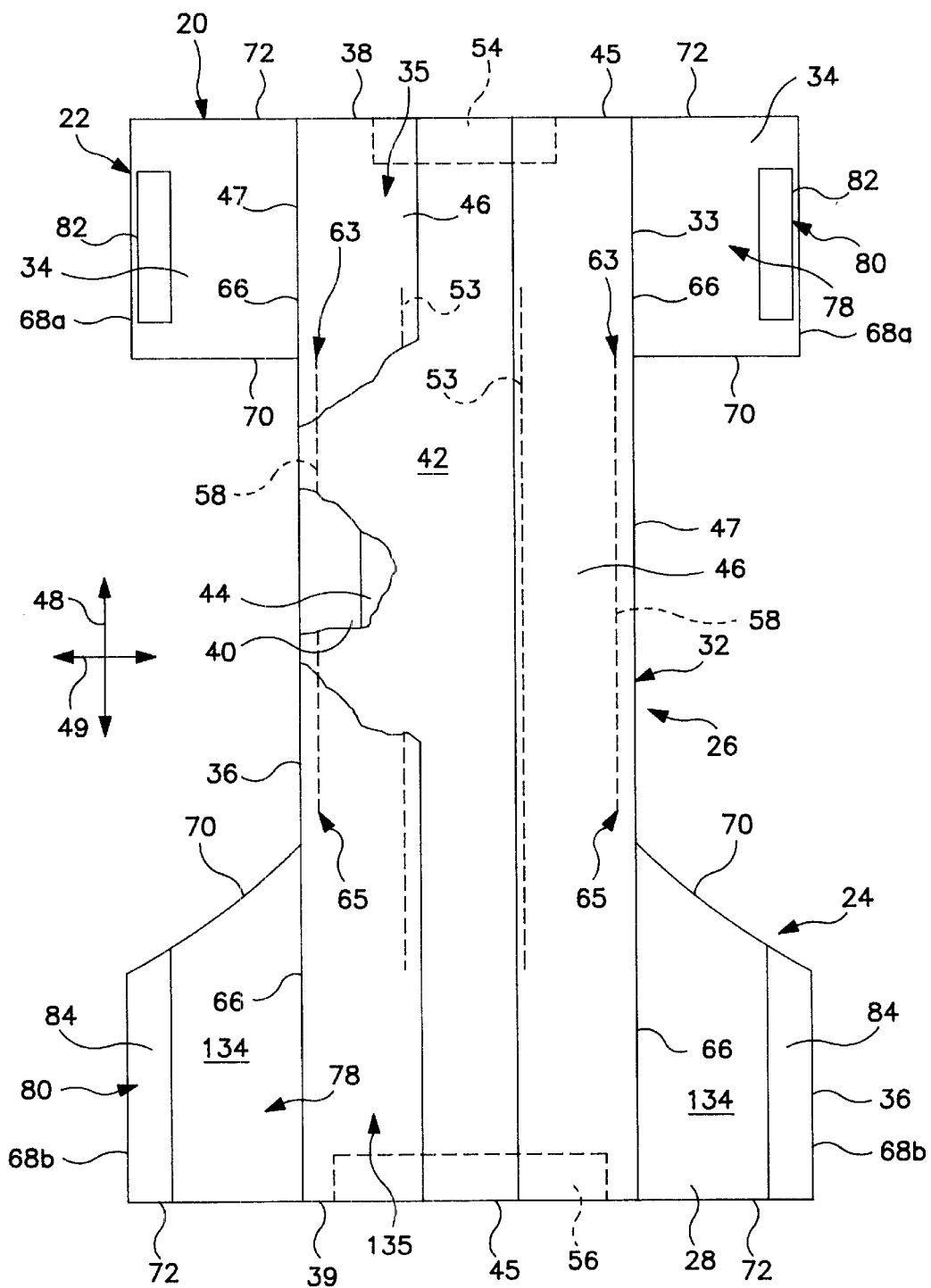
FIG. 3 is a plan view of an absorbent garment in a partially disassembled, stretched flat state, and showing the surface of the article that faces the wearer when the article is worn, and with portions cut away to show the underlying features.

"Cross direction assembly" refers to a process in which disposable absorbent products are manufactured in an orientation in which the products are connected side-to-side, in the transverse direction shown by arrow 49 in FIG. 3, a process utilizing a cross direction assembly entails products traveling through a converting machine parallel to the direction of arrow 49, as opposed to "machine direction assembly" in which the products are connected end-to-end or waist-to-waist.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearer's body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Longitudinal" and "transverse" have their customary meaning, as indicated by the longitudinal and transverse axes depicted in FIG. 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" which refers to the width of a fabric in a direction generally perpendicular to the machine direction.

"Machine direction assembly" refers to a process in which disposable absorbent products are manufactured in an orientation in which the products are connected end-to-end or waist-to-waist, in the longitudinal direction shown by arrow 48 in FIG. 3, a process utilizing a machine direction assembly entails products traveling through a converting machine parallel to the direction of arrow 48, as opposed to "cross direction assembly" in which the products are connected side-to-side.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Peel force" and "peel strain" refer to forces that tend to pull two adjoining bodies away from one another in opposite directions generally perpendicular to a plane in which the bodies are joined.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Shearing strain" refers to forces that tend to produce an opposite but parallel sliding motion between two bodies' planes.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a process for making a pant-like absorbent garment having refastenable fasteners, such as hook and loop fasteners, on the side panels for ease of removal and donning of the absorbent garment without complete removal of a wearer's clothing.

The principles of the present invention can be incorporated into any suitable disposable absorbent article. Examples of such suitable articles include diapers, training pants, feminine hygiene products, incontinence products, other personal care or health care garments, or the like. For ease of explanation, the description hereafter will be in terms of a child's training pant.

Figure 1:
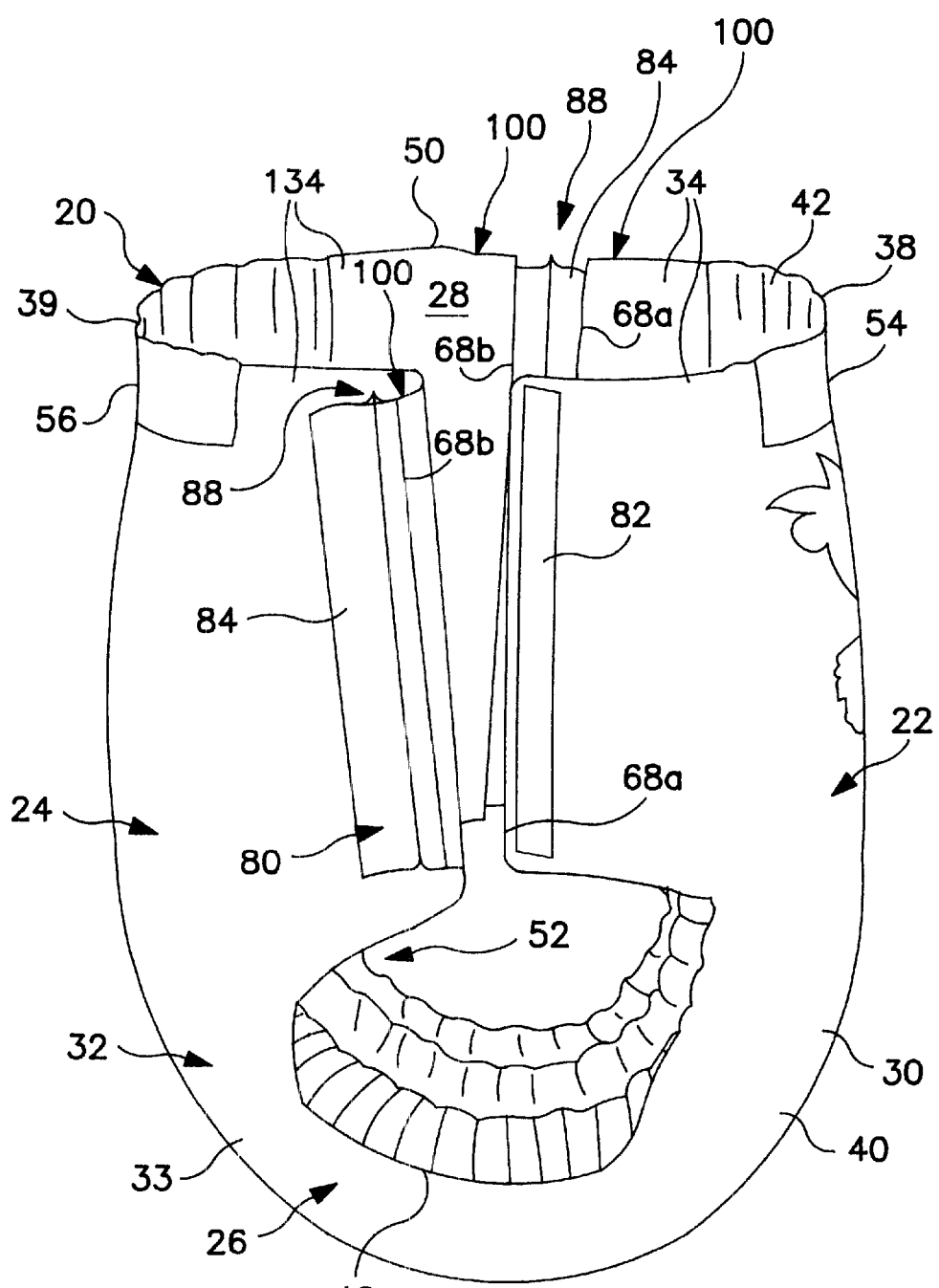
FIG. 1 is a side perspective view of an absorbent garment having dual refastenable sides and butt seams.

Referring to FIG. 1, a disposable absorbent article, such as a training pant 20, is illustrated in a partially fastened condition. The training pant 20 includes an absorbent chassis 32 and a fastening system 80. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

Figure 2:
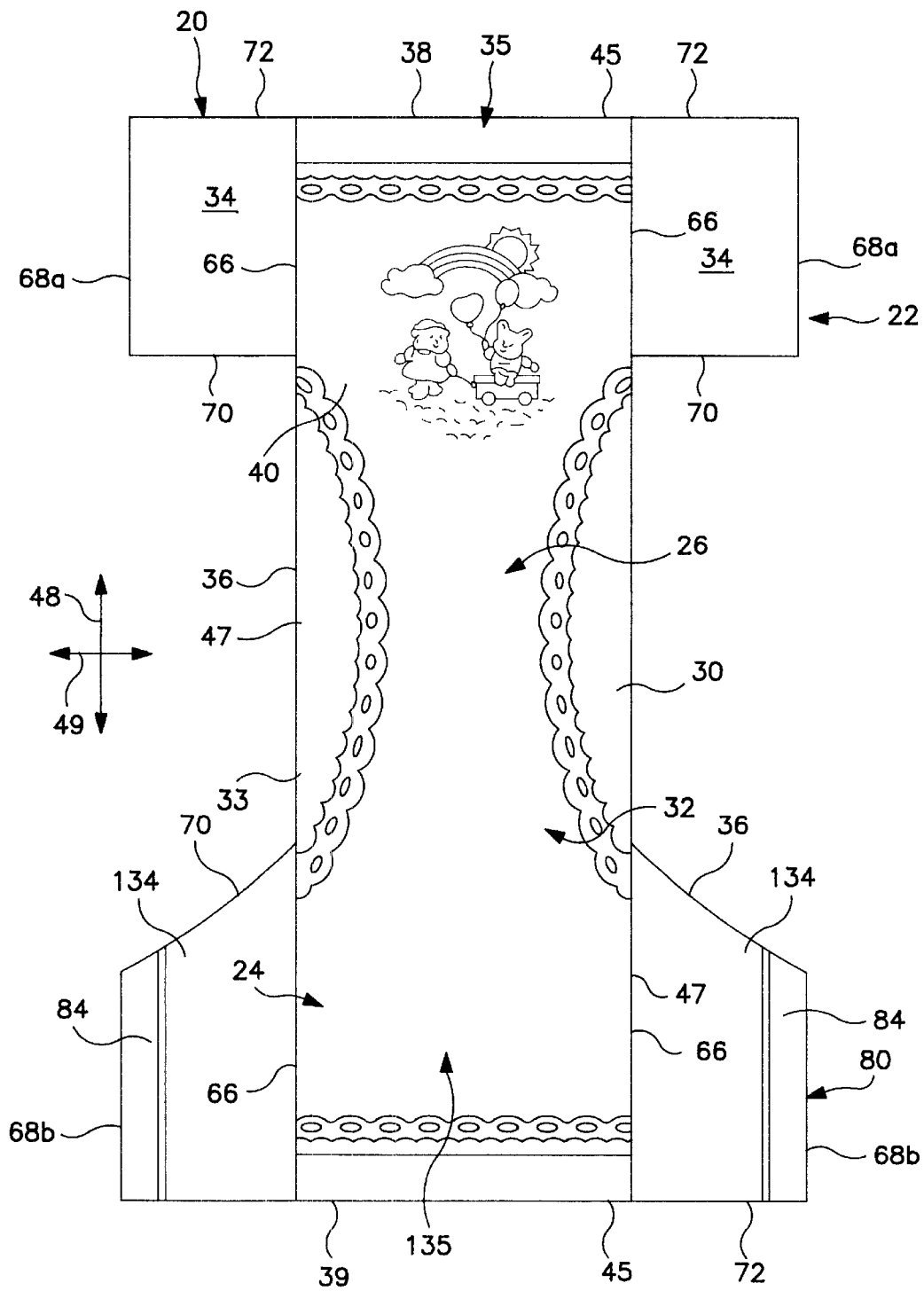
FIG. 2 is a plan view of an absorbent garment in a partially disassembled, stretched flat state, and showing the surface of the article that faces away from the wearer when the article is worn.

The illustrated absorbent chassis 32 includes a rectangular composite structure 33, a pair of transversely opposed front side panels 34, and a pair of transversely opposed back side panels 134. The composite structure 33 and side panels 34 and 134 may be integrally formed, as shown in FIG. 1, or may include two or more separate elements, as shown in FIGS. 2 and 3. The illustrated composite structure 33 includes an outer cover 40, a bodyside liner 42 which is connected to the outer cover in a superposed relation, an absorbent assembly 44 (FIG. 3) which is located between the outer cover 40 and the bodyside liner 42, and a pair of containment flaps 46 (FIG. 3). The rectangular composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front region 22 of the absorbent chassis 32 includes the transversely opposed front side panels 34 and a front center panel 35 (FIGS. 2 and 3) positioned between and interconnecting the side panels, along with a front waist elastic member 54 and any other connected components. The back region 24 of the absorbent chassis 32 includes the transversely opposed back side panels 134 and a back center panel 135 (FIGS. 2 and 3) positioned between and interconnecting the side panels, as well as a rear waist elastic member 56 and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily includes the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E. I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyoletin film commercially available from 3M Company, Minneapolis, Minn.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like, The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the composite structure 33 of the absorbent chassis 32 in the respective front and back regions 22 and 24, and are releasably attached to one another by a fastening system 80. More particularly, as shown best in FIGS. 2 and 3, the front side panels 34 can be permanently bonded to and extend transversely beyond the linear side edges 47 of the composite structure 33 in the front region 22 along attachment lines 66, and the back side panels 134 can be permanently bonded to and extend transversely beyond the linear side edges of the composite structure in the back region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover 40 or the bodyside liner 42, as shown in FIG. 1.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to a distal edge 68b of the back panel 134, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis 49 of the training pant 20. In particular embodiments, the front and back side panels 34 and 134 may each include an interior portion 78 disposed between the distal edge 68a, 68b and the respective front or back center panel 35 or 135. In the illustrated embodiment in FIG. 3, the interior portions 78 are disposed between the distal edges 68a, 68b and the side edges 47 of the rectangular composite structure 33. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or non-woven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIG. 1). The illustrated fastening system 80 includes fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

Figure 4:
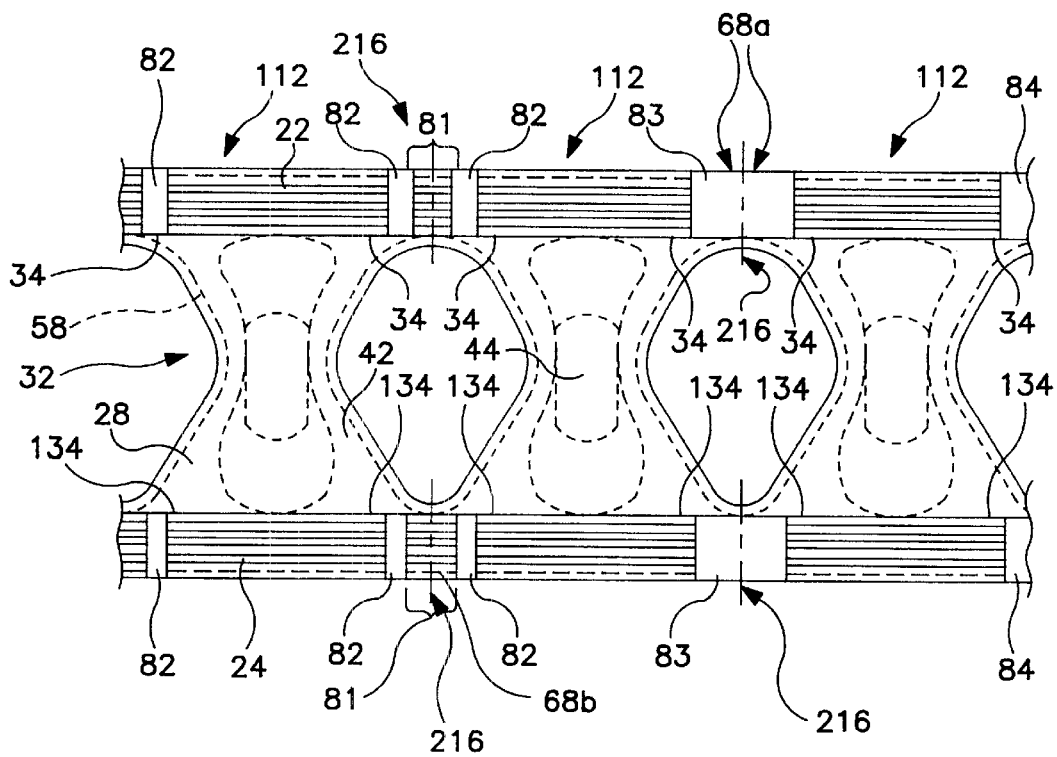
FIG. 4 is a plan view of a cross direction assembly for producing an absorbent garment having dual refastenable sides and butt seams.

With particular reference to FIG. 4, a plurality of garment assemblies 112 aligned in a cross direction is shown. The garment assembly 112 includes a lamination of films and nonwovens, including a bodyside liner 42 and an outer cover 40, together with waist elastics 54 and 56, leg elastics 58, and an absorbent assembly 44, as described above, placed on a vacuum device (not shown). Adjacent garment assemblies 112 are joined between the back side panel 134 and the front side panel 34. The exposed surface of the garment assembly 112 can be either the inner surface 28 of the chassis 32, as shown in FIG. 4, or the outer surface 30 of the chassis 32.

In carrying out the invention, two fastening components 82 are bonded to the back side panels 134 and two fastening components 82 are bonded to the front side panels 34 of each garment assembly 112, with a spacing 81 of roughly 0.25–1.0 inch between fastening components 82 on adjacent garments 20. Alternatively, a single, oversized fastening component 83 can be placed overlapping the planned locations of the distal edges 68a and 68b of two adjacent assemblies, to be separated into two fastening components 82 at the product cut-off stage. The fastening components 82 may include hook type fasteners or loop type fasteners, as described above.

Figure 6:
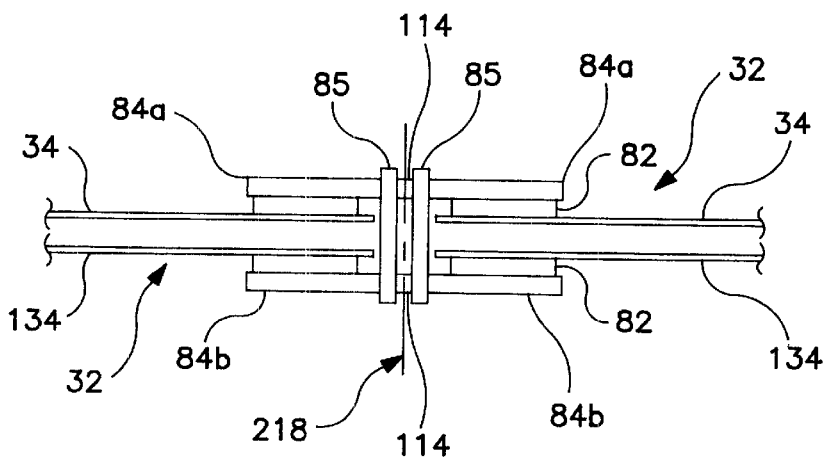
FIG. 6 is a top view of a fastening system during assembly in an absorbent garment having dual refastenable sides and butt seams.
Figure 7:
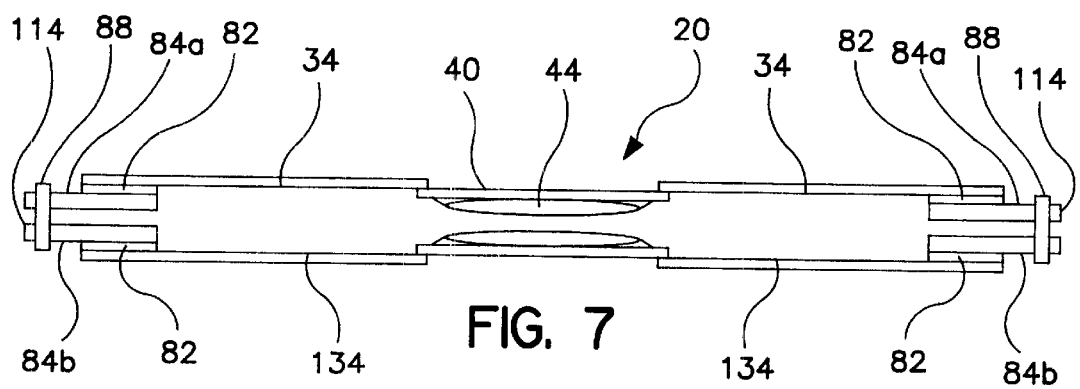
FIG. 7 is a top view of an absorbent garment having dual refastenable sides and butt seams.
Figure 8:
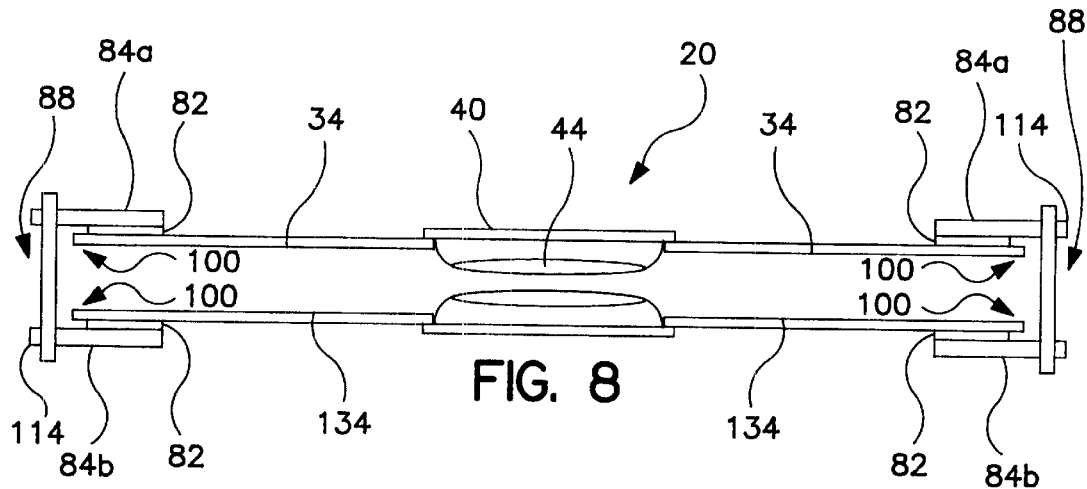
FIG. 8 is a top view of an absorbent garment having dual refastenable sides and butt seams.

After the fastening components 82 have been bonded to the garment assemblies 112, adjacent garment assemblies 112 are then separated by cutting along dotted lines 216 (FIG. 4). The adjacent garment assemblies 112 are spaced apart to provide room between the distal edges 68a and 68b of adjacent assemblies 112. A resulting gap (not shown) is provided in order to prevent the chassis or the fastening components 82 from being bonded together with the mating fastening components 84 when a standing butt seam 88 is formed, as shown in FIGS. 6–8. As used herein, the term "standing butt seam" refers to a seam wherein two separate pieces of substrate are bonded together face-to-face or back-to-back in close proximity to an outer edge of each of the pieces of substrate, and the outer edges of the pieces of substrate project outward from the finished product, placing the seam 88 in peel, as opposed to shearing strain. The mating fastening components 84 may include hook type fasteners or loop type fasteners, as described above.

When the assembly 112 is cut, the elastic property of the front side panels 34 and the back side panels 134 causes the front side panels 34 and the back side panels 134 to snap back from the cutting line 216 to the fastening components 82, maintaining the gap. Alternatively, a section of the adjoining front and back side panels 34, 134 between adjacent fastening components 82 can be cut out to maintain the aforementioned gap, thereby ensuring that each of the fastening components 82 is closely aligned with the corresponding resulting distal edge 68a, 68b. When an oversized fastening component 83 is used, which separates into two fastening components 82 when adjacent assemblies 112 are separated, a gap may then be created by the aforementioned snapping back of the front and back side panels 34, 134.

Two large patches of mating fastening components 84 are applied over the fastening components 82 of adjacent garment assemblies 112, thereby bridging the gap between the garment assemblies 112. All of the garment assemblies 112 connected by mating fastening components 84 are then folded in half lengthwise. The front mating fastening component 84a is then bonded, at bonding seam 85, to the back mating fastening component 84b along a distal edge 114 of each mating fastening component 84 outside of the chassis 32, as shown in FIG. 6. Adjacent garment assemblies 112 are then separated along cut line 218, thereby forming discrete products with standing butt seams 88, FIGS. 7 and 8.

Figure 5:
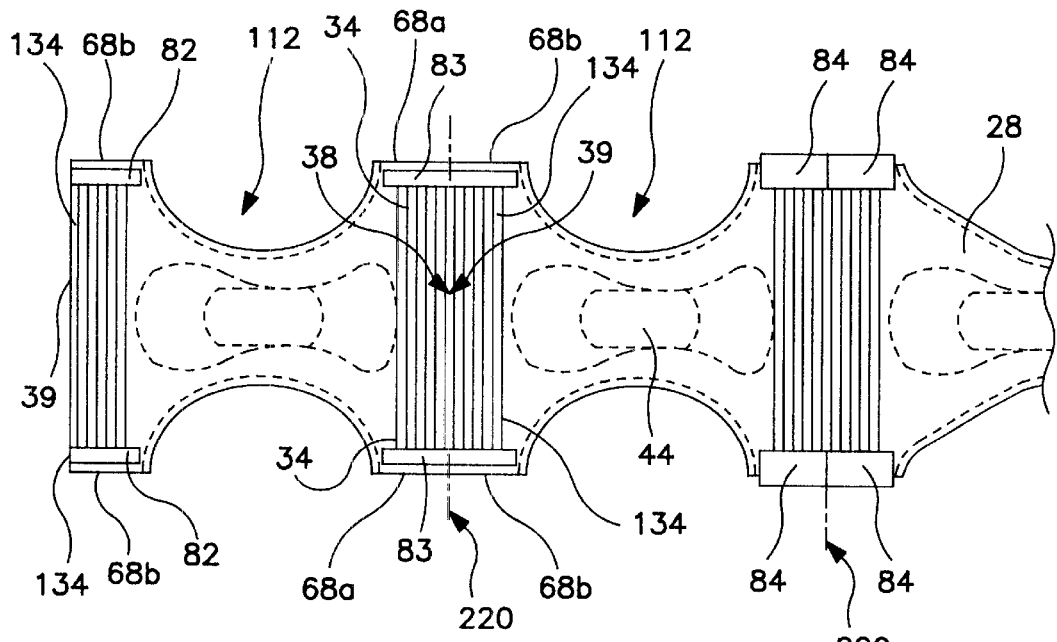
FIG. 5 is a plan view of a machine direction assembly for producing an absorbent garment having dual refastenable sides and butt seams.

The process of the invention can also be carried out in the machine direction, as shown in FIG. 5. As in the cross direction process, the exposed surface of the garment assembly 112 can be either the inner surface 28 of the chassis 32, as shown in FIG. 5, or the outer surface 30 of the chassis. In carrying out the invention, two fastening components 82 are bonded to the back side panels 134 and two fastening components 82 are bonded to the front side panels 34 of each garment assembly 112. Alternatively, two oversized strips of fastening components 83 can be applied to both the front side panel 34 and the back side panel 134 overlapping the planned locations of the front waist edge 38 and the back waist edge 39 of adjacent assemblies 112, to be separated at the product cut-off stage.

After the fastening components 82 have been bonded to the garment assembly 112 in the machine direction process (FIG. 5), four mating fastening components 84, wider than the fastening components 82, are aligned with and engaged with the fastening components 82, such that the mating fastening components 84 extend beyond the distal edges 68a and 68b of the garments. Similar to the fastening components 82, the mating fastening components 84 can be four separate components or can alternatively be oversized, and extend to cover the fastening components 82 on adjacent products. Adjacent garment assemblies 112 are then separated, along cut line 220 (FIG. 22), thereby also separating any extending fastening components 83 and/or mating fastening components 84. Each garment assembly 112 is then folded longitudinally, which aligns the mating fastening components 84 back-to-back with one another on either side of the garment, as shown in FIG. 7, or front-to-front with one another, as shown in FIGS. 6 and 8. The front mating fastening component 84a is then bonded to the back mating fastening component 84b along a distal edge 114 of each component outside of the chassis, thereby forming a standing butt seam 88, FIGS. 7 and 8.

As mentioned, the assembly procedures as illustrated in FIGS. 4 and 5 can be carried out with the fastening components 82 being bonded to either the inner surface 28 or the outer surface 30 of the assembly 112. The embodiment in FIG. 7 shows the resulting absorbent product 20 wherein the fastening components 82 are bonded to the inner surface 28. The embodiments in FIGS. 6 and 8 show the resulting absorbent product 20 wherein the fastening components 82 are bonded to the outer surface 30.

The product resulting from the invention is an absorbent product 20, shown in FIG. 1, having dual refastenable, prefastened hook and loop fasteners, oriented as lap side seams 100, along the distal edges 68a and 68b of the front and back side panels 34 and 134, with standing butt seams 88 between the lap side seams 100. The resulting orientation of the lap side seams 100 puts the prefastened seams under shearing strain during use, as opposed to peel forces. The term "lap side seam," as used herein, refers to a seam connecting the front and back side panels 34 and 134 or materials bonded thereto, such as fastening components 82 and 84, such that the front and back side panels and/or materials bonded thereto overlap and the seam is located between the distal edges 68a and 68b of the front and rear side panels 34 and 134.

The absorbent chassis 32 and the fastening system 80 together define a refastenable product having a waist opening 50 and a pair of leg openings 52. When the fastening system is engaged, it can be appreciated that the refastenable product includes a pair of elastomeric front side panels 34 extending from the waist opening 50 to each leg opening 52, a pair of elastomeric back side panels 134 extending from the waist opening 50 to each leg opening 52, a pair of standing butt seams 88, and two pairs of lap side seams 100 extending from the waist opening 50 to each leg opening 52 and positioned between the elastomeric front and back side panels 34, 134, an elastomeric front waistband 54 disposed on the front side 22 and positioned between the pair of elastomeric front side panels 34, an elastomeric back waistband 56 disposed on the back side 24 and positioned between the pair of elastomeric back side panels 134, and at least a pair of the leg elastic members 58 which partially encircle each leg opening 52. More preferably, more than one leg elastic member 58 partially or fully encircles each leg opening 52. Each leg elastic member 58 extends from adjacent an elastomeric front side panel 34 on the front side 22 to adjacent an elastomeric back side panel 134 on the back side 24.

As described herein, the various components of the absorbent garment 20 can be integrally assembled together employing various types of suitable attachment means, such as adhesive, sonic and thermal bonds or combinations thereof The resulting product is an absorbent garment having refastenable side seams that can be opened for donning or removal at either side of the garment.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of producing refastenable side seams in an absorbent garment, comprising the following sequence of steps:

aligning a plurality of garment assemblies in a cross direction, each garment assembly including a chassis with two back side panels and two front side panels, wherein adjacent garment assemblies are joined between a back side panel and a front side panel;

bonding a fastening component to each of the back side panels and each of the front side panels of each garment assembly;

separating adjacent garment assemblies from one another by cutting between the joined back side panels and the joined front side panels;

spacing apart adjacent garment assemblies, creating a gap between the fastening components of adjacent garment assemblies;

applying a mating fastening component over each fastening component;

folding the garment assemblies such that the mating fastening components on the front side panels are in contact with the mating fastening components on the back side panels; and bonding the mating fastening components on the front side panels to the mating fastening components on the back side panels.

2. The method of claim 1, further comprising the step of placing the plurality of garment assemblies on a vacuum device in the cross direction.

3. The method of claim 1 wherein the fastening components are bonded to an inner surface of the garment assemblies.

4. The method of claim 1 wherein the fastening components are bonded to an outer surface of the garment assemblies.

5. The method of claim 1 wherein the gap between the fastening components of adjacent garment assemblies is between about 0.25 inch and about 1.0 inch.

6. The method of claim 1, further comprising the steps of bonding an oversized fastening component to the joined front side panels of adjacent garment assemblies, and separating the oversized fastening component into two fastening components when the adjacent garment assemblies are separated from one another.

7. The method of claim 1, further comprising the steps of bonding an oversized fastening component to the joined back side panels of adjacent garment assemblies, and separating the oversized fastening component into two fastening components when the adjacent garment assemblies are separated from one another.

8. The method of claim 1, further comprising the step of cutting out a section of each of the joined front side panels and the joined back side panels to create the gap between the fastening components of adjacent garment assemblies.

9. The method of claim 1, further comprising the steps of applying an oversized mating fastening component over the gap and the fastening components of adjacent garment assemblies, and separating the oversized mating fastening component into two mating fastening components.

10. The method of claim 1 wherein the step of bonding the mating fastening components on the front side panels to the mating fastening components on the back side panels results in standing butt seams.

11. The method of claim 1 wherein the fastening component comprises a hook material and the mating fastening component comprises a loop material.

12. The method of claim 1 wherein the fastening component comprises a loop material and the mating fastening component comprises a hook material.

* * * * *